United States Patent [19]

Frant

[11] Patent Number: 4,504,790
[45] Date of Patent: Mar. 12, 1985

[54] APPARATUS AND METHOD FOR DETERMINING THE WATER CONTENT OF A WATER-CONTAINING MIXTURE

[75] Inventor: Martin S. Frant, Newton, Mass.

[73] Assignee: The Foxboro Company, Foxboro, Mass.

[21] Appl. No.: 308,312

[22] Filed: Oct. 5, 1981

[51] Int. Cl.³ ............................................. G01N 27/02
[52] U.S. Cl. ..................................... 324/439; 324/441
[58] Field of Search ............... 324/439, 441, 446, 450, 324/65 R, 428, 429; 210/351

[56] References Cited

U.S. PATENT DOCUMENTS

| 2,509,303 | 5/1950 | Jellinek | 324/439 |
| 3,971,980 | 7/1976 | Jungfer et al. | 324/428 |
| 4,322,685 | 3/1982 | Frailing et al. | 324/429 |

Primary Examiner—Michael J. Tokar
Assistant Examiner—Kevin D. O'Shea
Attorney, Agent, or Firm—Terrence Martin; Jack H. Wu; William E. Meyer

[57] ABSTRACT

An apparatus for determining the proportion of water within a mixture of water and a water-miscible solvent includes means for increasing the electrical conductivity of the mixture in proportion to the amount of water contained therein. In a particular embodiment this is done by passing a component stream of the sample through a replenishable bed of a salt, which salt is easily soluble in water but is relatively insoluble in the solvent. The dissolving of the salt introduces an appreciable number of conductive ions into the mixture, thereby enhancing its overall conductivity. A conventional detecting scheme measures the enhanced conductivity of the mixture, and means is provided for correlating this conductivity measurement to the proportion of water within the mixture.

6 Claims, 5 Drawing Figures

APPARATUS AND METHOD FOR DETERMINING THE WATER CONTENT OF A WATER-CONTAINING MIXTURE

BACKGROUND OF THE INVENTION

The present invention relates generally to a system for detecting the water content of a liquid mixture, and more particularly to a system which does so by enhancing the contribution of the electrical conductivity of the water to the overall conductivity of the mixture.

Generally, the quantitative determination of the water content of a multi-component liquid system can be done in a variety of ways, such as by titration with anhydrous reagents. However, the standard textbook procedures for such a determination generally are performed in a laboratory setting, under carefully controlled conditions. Therefore, they are not readily amenable to an on-line situation in which a rapid and accurate measurement is needed in a brief period of time, in less than ideal environments. A particularly critical application, and one which is gaining more attention due to the current world energy crisis, is the production of anhydrous (water-free) alcohol (usually ethanol) for combining with gasoline to produce gasohol. Since the presence of even the slightest amounts of water in the alcohol may have adverse effects on the performance of an engine, careful steps must be taken to ensure that all traces of water are eliminated from the final product before it is combined with the gasoline. Guaranteeing this water-free condition usually requires almost continuous monitoring of the output of the alcohol distillation column, and in such a situation the simplicity and fast response of the measurement scheme may be vital to achieving products within specification.

It has long been known that electrical conductivity can provide an accurate indication of the presence of water in mixed systems, and capacitance measurements have been used to detect water in jet fuels (kerosene). In fact, the use of conductivity measurements for detecting the presence of water is cited in an article entitled "Methods for the Determination of Water," by John Mitchell, Jr., included in *Handbook of Analytical Chemistry*, L. Meites, editor, McGraw-Hill, 1st edition, 1963. However, the cited article also comments that the presence of other conducting substances in variable amounts acts as an "interference," to hinder accurate measurement. Additionally, in the case where water is combined with alcohol, particularly ethanol or methanol, or with certain other water-miscible liquids, it is well known that a substantial change in the water content has only minimal effect on the overall conductivity of the combined liquids. The following Table I derived from direct conductivity measurements of ethanol and water solutions shows the minute changes in conductivity produced by changes in the water content:

TABLE I

| Conductivity of Ethanol/Water Mixtures as a Function of Water Content | |
|---|---|
| % Water | Conductivity (microsiemens/cm) |
| 0 | 0.82 |
| 1.25 | 0.83 |
| 2.50 | 0.85 |
| 3.75 | 0.88 |
| 6.25 | 0.91 |

A five-fold increase in water content, from 1.25 to 6.25 percent, yields only a 0.08 microsiemens/cm change. This extremely small change has made the direct measurement of conductivity an impractical indicator of water content in the past. It should be noted that this deficiency is even more pronounced when the water and alcohol systems being measured are in the range of 99-plus percent alcohol, since a fraction of a percent change in the water content produces an almost negligible change in the overall conductivity of the system.

Therefore, it is an object of the present invention to provide a method and apparatus for making practical on-line determinations of water content by means of a conductivity measurement, in an accurate and timely manner.

SUMMARY OF THE INVENTION

An embodiment of an apparatus for determining the proportion of water within a mixture containing water and a watermiscible organic solvent, in accordance with the present invention, includes a first stage which increases the electrical conductivity of the mixture by an amount which is related to the water content of the mixture. A second stage measures the electrical conductivity of the mixture, after the conductivity of the mixture has been increased. The final stage relates the conductivity measurement to the proportion of water within the mixture.

In accordance with a specific embodiment of the invention, a sample portion of the liquid mixture being tested is allowed to interact with an excess quantity of a water-soluble ionizing salt. The salt has the property that its solubility within the organic solvent is insignificant compared to its solubility within the water. As a result of the interaction with the salt, the sample's conductivity increases. It is believed that this increase is primarily a function of the solubility of the salt in the mixture, but it also may be related to the extent of ionization of the salt therein. The measurement of this increased conductivity can be correlated to a water percentage reading by the use of an empirically developed calibration curve corresponding to the particular solvent and salt in use. The correlation can be done quite simply, for example, by calibrating the scale on the conductivity meter output indicator in terms of water percentage, rather than the standard conductivity or resistivity readings.

Although there is a wide variety of ionizing salts that are soluble in water, for a salt to be particularly effective in this embodiment, it should satisfy four basic criteria. First, there must be a significantly higher solubility of the salt in water than in the organic solvent. Second, the total solubility within the liquid system as a whole should be relatively small, to insure that minimal amounts of salt are consumed. Third, it is desirable that the salt should not be toxic so that the sampled liquid can be recycled without preliminary treatment or waste. Fourth, it would be desirable for the solubility to have a low temperature coefficient, so that extensive and precise temperature control is not required.

In an alternate embodiment of the invention the apparatus is made applicable to a liquid system in which there are two organic solvents mixed with water into a single liquid phase. For example, the invention can be utilized with a system containing two water-miscible solvents, such as the azeotrope of acetonitrile and ethanol, which typically contains about one percent water. The invention also is usable with systems in which one of the two solvents is water-immiscible, but the range of solvent compositions is limited, since the presence of the dissolved salt may cause phase separation. Such separation occurs in certain composition ranges of the tertiary mixture of water, benzene and ethanol, although at other ranges, the system remains miscible and permits a meaningful conductivity measurement to be made which can be correlated to the water content.

BRIEF DESCRIPTION OF THE DRAWINGS

The novel aspects and distinct advantages of the present invention will be make clear by the following detailed description, in conjunction with the accompanying drawings, in which.

DESCRIPTION OF THE PREFERRED EMBODIMENT

Figure 1:
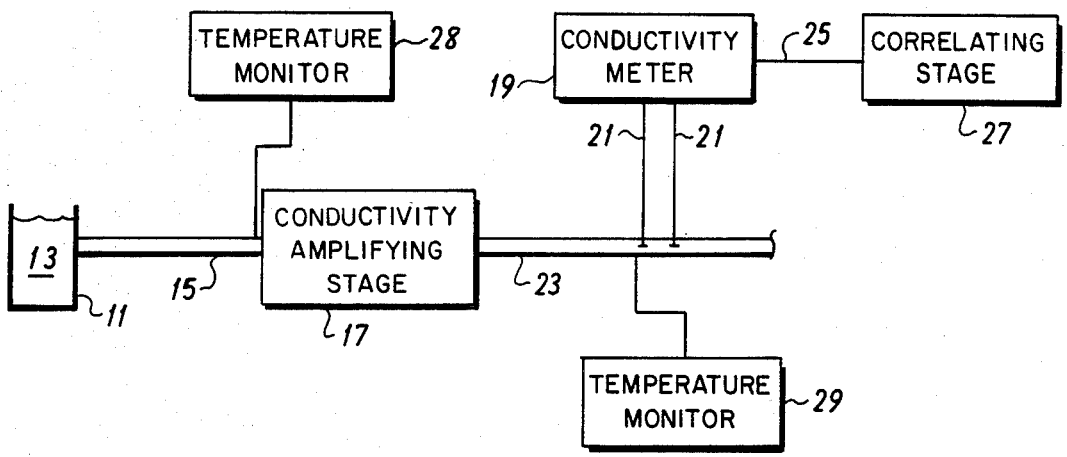
FIG. 1 is a block diagram of a water content measuring system in accordance with the present invention.

In FIG. 1 a reservoir 11 contains a quantity of a liquid mixture 13, comprising a water-miscible organic solvent, such as ethanol or methanol, and an unknown percentage of water. In a particularly useful application of the present invention the reservoir can represent part of an alcohol distillation column in which the production of 99-plus percent ethanol is desired. A small sample quantity of the liquid is drawn off from the reservoir by a sample line 15, on either an incremental or a continuous basis, as the situation dictates. The sample is introduced into a conductivity amplifying stage 17, which operates to enhance the conductivity of the sample in accordance with the amount of water present in the sample. As discussed above, normally the conductivity of an ethanol and water mixture does not change, to any easily mesurable extent, with variations of the water content of the mixture. However, because of the conductivity multiplying factor produced by the amplifying stage 17, changes in water content become easily discernible.

A conductivity meter 19, a device well known to the art, has its detecting electrodes 21 in contact with the fluid stream at a point within a discharge conduit 23. The conductivity meter provides an output indication which is a direct measurement of the electrical conductivity of the mixture, and typically is presented in units of conductivity, or its inverse, resistivity. Representative of such a conventional unit is the Model 910 Conductivity Monitor, manufactured by The Foxboro Company. The output of the conductivity meter is supplied via a line 25 to a stage 27 which correlates the conductivity reading to a percentage of water reading. A more detailed description of this correlating stage is provided hereinafter. After passage through the discharge conduit 23, the sample liquid can either be discarded as waste, or be recycled by being reintroduced into the reservoir 11.

Temperature monitors 28, 29 sense the temperature of the sample during its passage through the amplifying stage 17 and at the time of the conductivity measurement, respectively. An awareness of the temperatures at these locations allows compensation to be made in the water content reading, for changes, with temperature, of both the amount of conductivity amplification and the conductivity itself.

Figure 2:
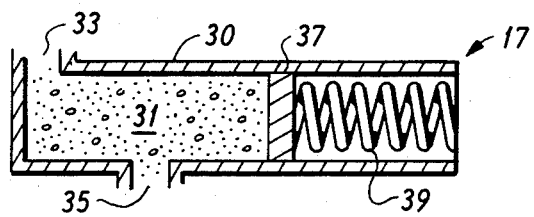
FIG. 2 is a cross-sectional view, in diagrammatic form, of an embodiment of the conductivity-amplifying stage of the system of FIG. 1.

Referring now to FIG. 2, a particularly advantageous apparatus for use as the conductivity amplifying stage 17 is shown, in which chemical procedures are used to enhance the conductivity of the water component. The term "chemical" is being used here in the sense of changing the composition of the mixture by the addition of a chemical thereto. A housing 30 contains a bed of a salt 31, which salt has the properties of (a) producing electrically conductive ions when dissolved in water, and (b) of being appreciably more soluble within water than it is within the solvent with which the water is mixed. In the case of an ethanol and water mixture, the following salts are found to be particularly useful: sodium chloride (NaCl), potassium nitrate ($KNO_3$), and potassium chloride (KCl), with potassium chloride having the best characteristics. In the case of a methanol and water mixture, sodium sulfate ($Na_2SO_4$) is especially suitable. The housing has a sample inlet port 33 which accepts the sample stream drawn from the reservoir 11. The sample flows through and interacts with the salt and exits at an output port 35 which communicates with the discharge conduit 23 (see FIG. 1).

Figure 3:
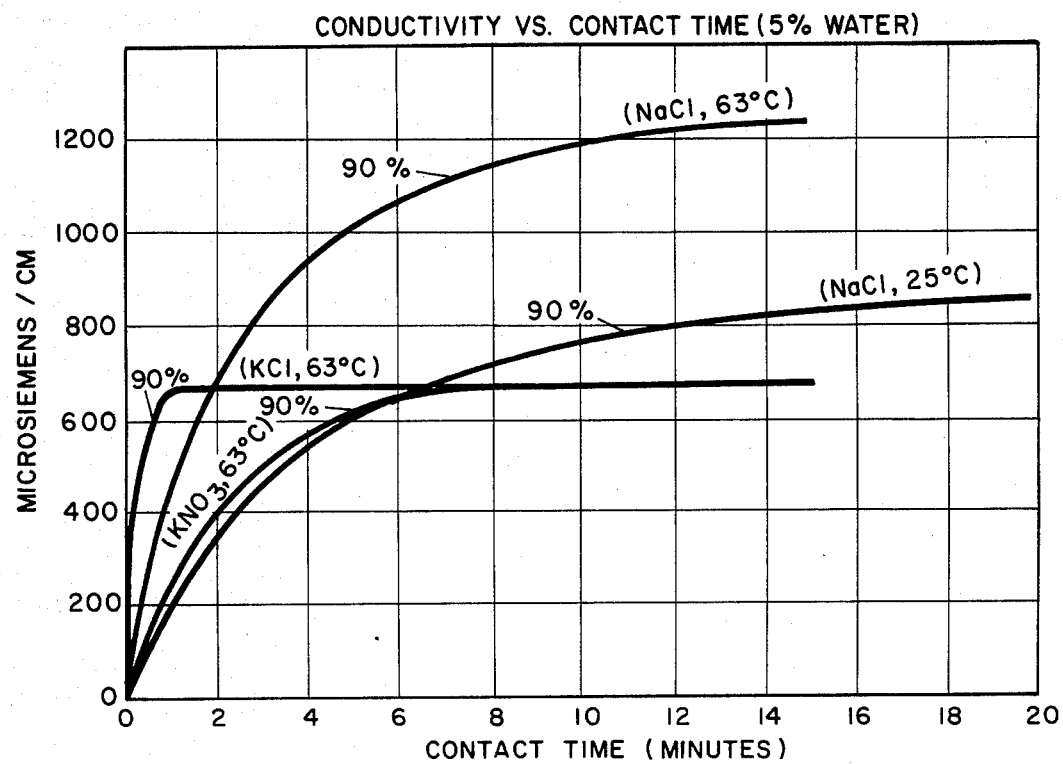
FIG. 3 is a graph illustrating typical contact times of various salts in a 5-percent water/95-percent ethanol solution.

It should be noted that the total amount of the salt which is dissolved by the water depends on, among other factors, the length of time in which the sample and the particular salt are allowed to interact. For any given "contact time," this amount of salt varies with temperature, and also with the concentration of water within the sample, since the rate of solubility itself is concentration-dependent. Preferably the salt and the liquid sample should be allowed to interact until the sample is saturated and an equilibrium condition is achieved. However, to shorten the contact time, a level equal to 90-percent of saturation may be used. Typical values of contact time necessary to reach this 90-percent level in a 5-percent water/95-percent ethanol solution are as follows: KCl at 63° C., 0.6 minutes; $KNO_3$ at 63° C., 4.8 minutes; NaCl at 63° C., 7.0 minutes; and NaCl at 25° C., 10.8 minutes. These values are depicted graphically in FIG. 3. In any case where saturation is not being achieved, such as in this 90-percent example, both the rate of flow of the sample through the salt bed and the amount of surface area at the salt-to-liquid interface must be coordinated, to provide a contact time appropriate for the temperature of the sample liquid and for the particular salt being used.

Referring again to FIG. 2, a movable piston 37 is biased toward the left-hand end of the housing 30 by a spring 39 to maintain a constant pressure against the salt bed 31. This serves to keep the salt tightly compacted so as to maintain a constant amount of surface area at the salt-to-liquid interface, and to prevent channeling as the liquid courses through the salt. The piston also provides an automatic shut-off feature, because as the salt is consumed and dwindles down to a critically low level, the piston eventually will block the outlet port 35, and interrupt the free flow of the sample.

Figure 4:
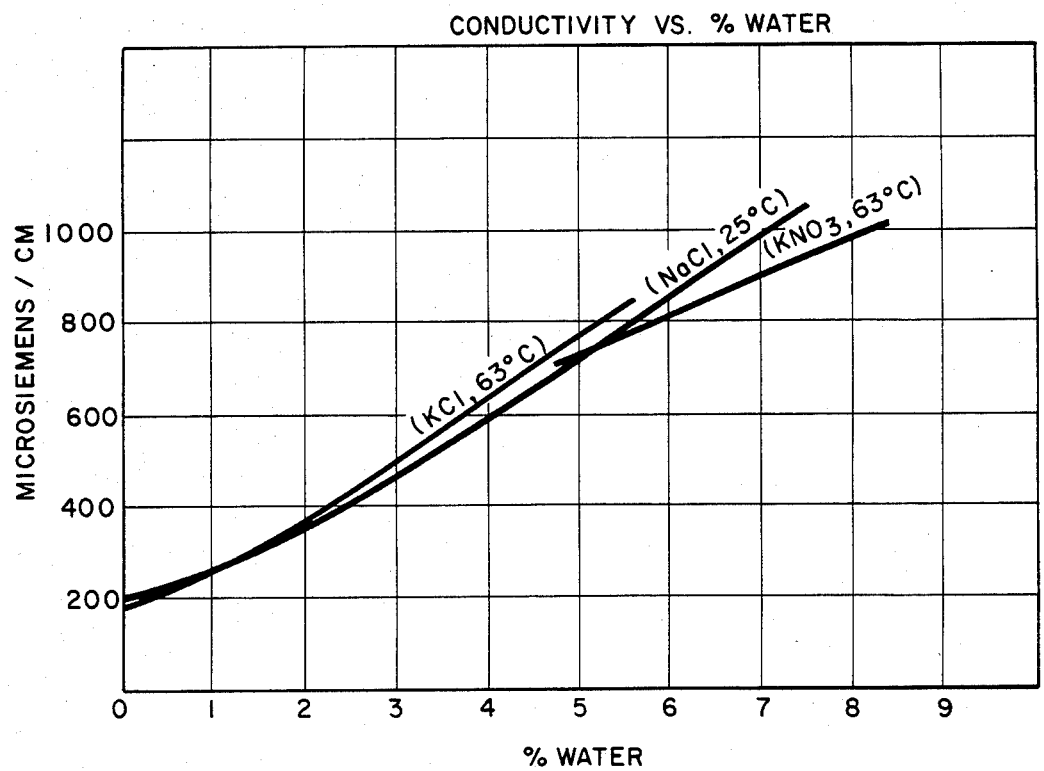
FIG. 4 is a representative group of conductivity-versus-water concentration calibration curves.

As mentioned above with the reference to FIG. 1, once a conductivity measurement has been obtained, it must be correlated to a reading indicative of the water content of the mixture. When the conductivity has been amplified by addition of a water-soluble salt, this correlation can be performed with the aid of empirically generated calibration curves, such as those shown in FIG. 4. These representative curves depict, for potassium nitrate, potassium chloride, and sodium chloride respectively, the change in conductivity of an ethanol and water solution with changes in the percentage of water, at a specified reference temperature. These curves are developed by a "standard addition" method, in which a first conductivity reading is taken in a solvent which is as dry as possible and contains a large excess of undissolved salt. Subsequent conductivity readings are taken after the addition of standard quantities of water, with adequate salt present to maintain saturation of the mixture. This procedure was used to produce the data for the curves of FIG. 4. Although the curves shown are developed for a single temperature, it is apparent that a family of calibration curves, each corresponding to a different temperature, may be generated for the particular salts and the particular solvents in use.

A simple method for incorporating the information within these curves into a device which directly reads out water content of the sample is by recalibrating the indicating scale of the conductivity meter 19 in terms of water percentages rather than the usual microsiemens/cm conductivity units. Of course, the curve used for recalibration must be appropriate for the temperature at which the measurement is taken. Alternatively the correlating stage 27 may consist of electronic circuitry, evident to those skilled in the electronics arts, which can generate a water percentage output reading in response to conductivity and temperature inputs from the conductivity meter 19 and the temperature monitor 29 respectively. For instance, such circuitry may include a microprocessor with an appropriate lookup table stored in its memory, the lookup table containing data derived from the appropriate family of calibration curves (see FIG. 4). Clearly the need for temperature compensation, in light of the various temperature dependencies, can be avoided by maintaining controlled temperatures both at the point at which the salt is added to the liquid sample, and at the point at which the conductivity measurement is made. Preferably, the two temperatures will be identical. However, such temperature control can be accomplished in any one of several conventional control schemes, and will not be dealt with in detail in this application.

Figure 5:
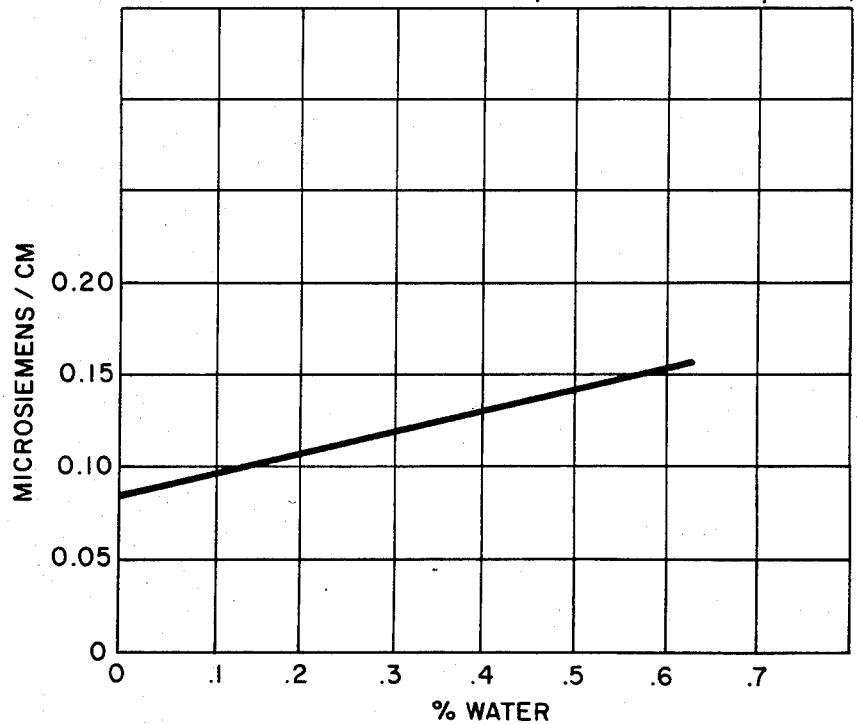
FIG. 5 is a calibration curve for a three-component liquid system.

Although all of the foregoing has been discussed in the context of a two-component, single liquid phase system, namely water mixed with a single organic solvent, nevertheless it is possible to apply the teachings of the present invention to a system in which more than one organic solvent is present, providing both of them mix with the water to form a single liquid phase. Such a situation can occur with an ethanol, benzene and water system, such as is found in an azeotropic ethanol distillation column. Experimentation has shown that for particular proportions of ethanol, benzene and water, a salt, most notably sodium-EDTA, can be added to enhance the conductivity without causing the benzene and ethanol to separate into different phases. The phase separation typically occurs in the form of an alcohol/water layer and a predominantly benzene layer. As long as the single phase nature is maintained, the teachings of the present invention are applicable. However, once phase separation has occurred, the scheme of the present invention is inapplicable. FIG. 5 shows the variation, with small amounts of water, in the conductivity of a system initially containing 70 percent benzene and 30 percent ethanol, using sodium EDTA as the ionizing salt. This calibration curve provides the same type of conductivity-to-water content correlation for a three-component liquid system as the curves of FIG. 4 do for a two-component system. If both of the two liquid solvents are water-miscible, as is the case with the azeotrope of acetonitrile and ethanol, then phase separation is not a problem. In such a case, the present invention can be practiced over a virtually unlimited range of compositions of the two solvents and water, and calibration curves can be generated by techniques analogous to those described with reference to FIG. 4.

Although the present invention has been described in terms of a preferred embodiment, as shown in the accompanying figures, certain modifications and changes will become apparent to those skilled in the art. For example, while the amplification of the conductivity has been described by means of the addition of water-soluble salts, alternate schemes for increasing the ionic population of the sample and thereby increasing its conductivity, may be equally feasible. Such alternate schemes may include the use of ionizable gases, e.g., $CO_2$ or $HCl$, in place of the salts, or even the use of non-electrochemical procedures. Similarly, any one of a variety of electronic circuits for correlating the conductivity measurement to the percentage of water can be envisioned, which would be adaptable to the purpose of the present invention. Nevertheless, it is intended that such modifications be encompassed within the scope of the following appended claims.

What is claimed is:

1. Apparatus for determining the proportion of water within a mixture containing water and ethanol, comprising:
   a housing containing a bed of an ionizable, water-soluble salt, said salt being relatively insoluble in ethanol, relative to its solubility in water, and said housing having inlet and outlet ports to permit said mixture to flow through said salt;
   a spring-biased piston located within said housing and disposed to bear against said bed of salt, so as to keep said salt tightly compacted;
   means coupled to said outlet port for measuring the electrical conductivity of said mixture after it has flowed through said bed of salt; and
   means for relating the measured conductivity to the proportion of water in the mixture.

2. Apparatus as set forth in claim 1, wherein said relating means comprises means for deriving from a conductivity-versus-water percentage calibration curve for the combination of said mixture and said salt a water percentage value corresponding to said measured conductivity.

3. Apparatus as set forth in claim 2, wherein said salt is potassium chloride (KCl).

4. Apparatus as set forth in claim 2, wherein said salt is sodium chloride (NaCl).

5. Apparatus as set forth in claim 2, wherein said salt is potassium nitrate ($KNO_3$).

6. Apparatus for determining the proportion of water within a mixture containing water, ethanol, and benzene, comprising:
   means for increasing the electrical conductivity of the mixture by introducing sodium-EDTA salt into the mixture, thereby increasing the ion population of the water;
   means for measuring the increased electrical conductivity of the mixture; and
   means for relating the measured conductivity to the proportion of water in the mixture.

* * * * *